United States Patent [19]
Reid et al.

[11] Patent Number: 4,476,386
[45] Date of Patent: Oct. 9, 1984

[54] METHOD AND APPARATUS FOR MATERIAL ANALYSIS

[75] Inventors: Alan F. Reid, Hawthorn; Martin A. M. Zuiderwyk, North Balwyn, both of Australia

[73] Assignee: Commonwealth Scientific and Industrial Research Organization, Australia

[21] Appl. No.: 380,865

[22] PCT Filed: Jun. 10, 1981

[86] PCT No.: PCT/AU81/00071
§ 371 Date: Jan. 26, 1982
§ 102(e) Date: Jan. 26, 1982

[87] PCT Pub. No.: WO81/03707
PCT Pub. Date: Dec. 24, 1981

[30] Foreign Application Priority Data
Jun. 11, 1980 [AU] Australia ............................. PE3998

[51] Int. Cl.³ .................. G01N 23/223; G01N 23/225
[52] U.S. Cl. ..................................... 250/310; 250/307
[58] Field of Search ................................ 250/307, 310

[56] References Cited

U.S. PATENT DOCUMENTS 3,204,095 8/1965 Watanabe ............................ 250/310
3,351,755 11/1967 Hasler ................................. 250/307
3,909,612 9/1975 Gibbard .............................. 250/307
4,288,692 9/1971 Schamber et al. ................... 250/310

Primary Examiner—Alfred E. Smith
Assistant Examiner—Jack I. Berman
Attorney, Agent, or Firm—Sughrue, Mion, Zinn, Macpeak & Seas

[57] ABSTRACT

Method and apparatus for material analysis in which X-rays generated pursuant to incidence of an electron beam on the material are detected by a detector which generates signals representative of X-ray intensity. A first single analyzer is connected to receive the signals from the detector and to pass to an associated first counter a count signal whenever the signal applied to the first single channel analyzer is representative of an X-ray energy within a relatively narrow range of such energies. A second single channel analyzer is also connected to receive the signals from the detector and to pass to an associated second counter a count signal whenever the signal applied to the second analyzer is representative of an X-ray energy falling within a much broader range of such energies than the first mentioned range. The first and second counters accumulate the count signals applied thereto. The count in the second counter is compared by a comparator with a pre-established count in a third counter and when the count in the second counter assumes the same value as the count in the third counter the counts in the first and second counters are held. The so held count in the first counter then itself represents a normalized ratio of X-ray energy within the narrow range to the X-ray energy for the energy spectrum represented by the broad range of energies. On the basis of this normalized ratio information as to the makeup of the material can be derived.

42 Claims, 7 Drawing Figures

METHOD AND APPARATUS FOR MATERIAL ANALYSIS

This invention relates to a method and apparatus for material analysis of the kind in which a beam of energy is caused to fall on a spot on the surface of the sample of material to be analysed and signals, such as X-ray signals or backscattered electron signals are generated each representing an effect of the beam at the spot and from which signals information as to the makeup of the material can be derived.

Methods of the above kind are adapted for use where a scanning electron microscope provides the beam of energy and it is principally in this context that the invention is particularly described thereinafter. However, the invention is not confined to use of scanning electron microscopes.

The invention broadly contemplates, in one aspect, a method of analysis in which a beam of energy is caused to fall on a spot on the surface of a sample to be analysed and X-rays then generated at the spot are detected by one or more detectors to produce first signals representative of the energies of detected X-rays; a first count of the number of said first signals each representative either of an energy within a relatively broad range of such energies or of a combination of discrete energy intervals across said first relatively broad range said combination including coincident, anti-coincident or contiguous intervals being made and a second count of the number of said first signals each representative of one particular energy or of an energy in an associated relatively narrow range of energies about said particular energy being made, wherein information relating to the relative proportion of a particular chemical element, characterized by production of X-rays of or about of said particular energy is obtained in the form of a normalized ratio of said second count to said first count, said normalized ratio being represented by the value of said second count assumed when the said first count reaches a predetermined value. The first said count may as a particular case consist of the sum of all or some subset of the second said counts.

In another aspect, the invention broadly contemplates apparatus for material analysis including:

energy generating and directing means for causing a beam of energy to fall on a spot on the surface of a sample of the material to be analysed;

detector means for detecting X-rays generated at said spot and for producing first signals representative of the energies of detected X-rays;

first accumulating means coupled to accumulate a first count of the number of said first signals each representative either of an energy within a first relatively broad range of such energies or of a combination of discrete energy intervals across said first relatively broad range, said combination including coincident, anti-coincident or contiguous intervals;

second accumulating means for accumulating a second count of the number of said first signals each representative of one particular energy or of an energy in an associated relatively narrow range of energies about said particular energy;

presettable means coupled to said first accumulating means and responsive, on said first count reaching a predetermined value, to control said second accumulating means to hold the value of said second count then assumed, whereby said assumed value represents a normalized ratio of said second count to said first count which normalized ratio is dependent on the proportion of a particular chemical element in said sample.

In addition to the normalized value already notionally divided, an actual division can be carried out if desired and the results obtained therefrom may be further manipulated.

The invention is further described by way of example with reference to the accompanying drawings in which.

Figure 1:
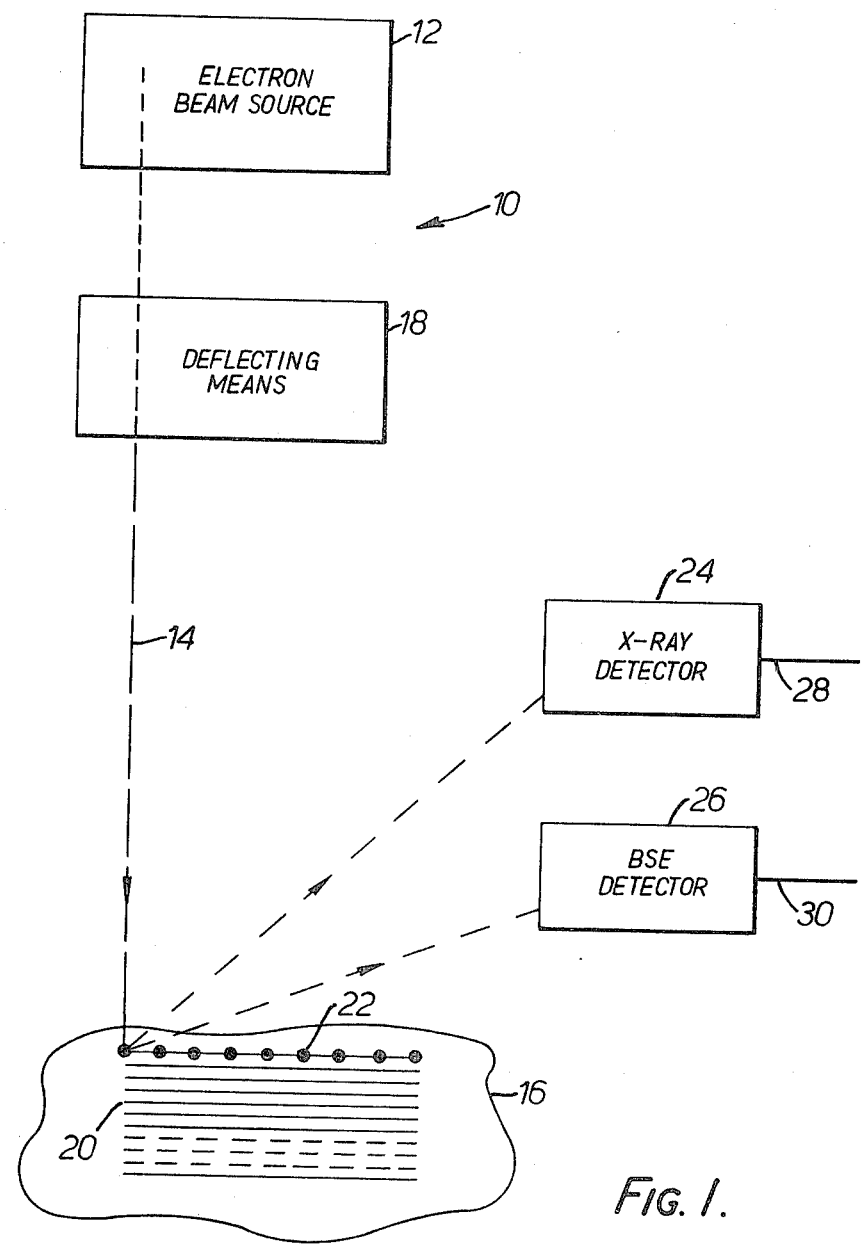
FIG. 1 is a diagram illustrating the use of a scanning electron microscope to obtain image information from a sample.

Generally, the aspects of the invention to be particularly described relate to an image acquisition and analysis system which, from a material sample, forms or allows to be formed, mineral, compositional, elemental or phase maps, or identifies at specified image points the phase, mineral composition, element or elements present at those points. The compositional map identifies in two dimensions the regions of different mineral or material composition. This map is formed in such a way that it may be readily stored in a minicomputer or in the bulk storage peripherals with which such a computer is fitted. The mode of map storage allows the ready treatment of the data to extract a large number of quantitative parameters describing the objects viewed in the scanning microscope field. These objects may be individual particles, and the particles may themselves contain a number of different species. Alternatively the sample may be a section of an ore or other material occupying the whole or part of the scanned field. The image acquisition system uses severally and in combination elemental X-rays and the secondary, backscattered or absorbed electron signals created for example when an electron beam, a collimated X-ray fluorescence beam, an ion beam or a proton beam falls on a defined spot on a sample. The set of such spots is defined as the image raster, and in general the beam of charged particles or protons which is creating X-ray, electron, or proton signals is moved or positioned in a regular pattern. The present invention allows elemental X-rays and backscatter electron signal intensities generated by the beam of a scanning electron microscope to be used to define the mineral, composition, phase or element present at each point. These signals may be processed preferably in real time to produce in a rapid manner a digital word or mask which defines, or serves to define, the mineral, composition, phase, or element at each point of the raster and to allow the formation of a map or image of these species separately or in combination, and the transmission to a computer or similar memory a condensed version of the data defining such a map or image, all of these procedures being accomplished during the actual scan of the sample or a defined region of it.

The sample may consist of a polished or moderately rough specimen or surface of an ore or rock, a metallurgical or ceramic material, or any similar or comparable material. Particles or fragments of such material may be cast in epoxy, plastic, or other media and the sample then consists of a section exposed by cutting through the casting. In particular, the sample may also consist of individual fragments or particles, placed on or adhering to a supporting surface, and across which the irradiating beam is moved or onto each of which it is directed.

The form of the invention to be described permits the formation of images in which the spatial location and correspondences between mineral, compositional, phase or elemental species are determined. The method may be used for initial location followed by quantitative analysis of specific minerals and phases, for example individual monophase particles or objects in a field of view, or for example regions consisting of a given mineral in particles or sections. Once the described interpretive procedure has located a specific or required phase, the electron beam may be redirected to it, and X-ray acquisition times long enough to allow quantitative analysis can be used. For example the iron content of sphalerite, $(Zn,Fe)S$, can be determined in this way after the species has been initially located and identified by the methods of the invention.

From compositional or species maps or images the procedures to be described can abstract stereological, spatial, textural or metric parameters or information regarding the objects or adjacent areas in the image or sample. The procedures also include modal analysis, as generally defined in quantitative minerology or metallography and the analysis of individual particles either in terms of their mapped compositional features or as monophase individuals.

The apparatus and methods to be described provide for the rapid real time accumulation of an image map, or of image lines or points, within which compositional species such as minerals, metallurgical phases, or individual elements are identified. The map, line or point data can be produced in a condensed form which minimizes data transfer from the image acquisition system to a memory device, such as the memory of a standard minicomputer, and provides an image data format which can be directly manipulated by algorithms which take maximal advantage of this condensed format. Compositional bit patterns for every point in a raster can also be transmitted or stored when required.

In the following description real time is defined to mean an event, decision or procedure carried out during the course of an operation, in particular during the process of positioning the irradiating beam at a sequence of spatially defined points so as to create a digital image raster or part thereof. Backscattered electron(s) is abbreviated to BSE, energy dispersive X-ray analyser or analysis to EDS. The embodiments of the invention to be described facilitate the formation of a map of a mineral section or of a large number of particles to be formed within a practical time, fractions of seconds for BSE signals alone, or minutes to tens of minutes for X-ray signals, and the subsequent treatment of this data in times of the order of seconds or minutes in order to describe quantitatively the properties of populations of composite particles, or of ore sections and of solid material samples generally.

Accumulation of the whole or part, or more than one part, of an EDS spectrum during a period just sufficient to provide a "yes" or "no" response to the presence or absence of a given element or group or set of elements may be effected, and the selection from within the various spectral regions of those groups of responses, e.g. successive memory or event counter locations, which serve to characterize each identifiable elemental X-ray, and the performance of an examination or decision on the contents of such groups or on the combinations of their contents, so as to provide a digital word or mask which characterizes the species or composition of the raster point from which the X-ray and BSE data is derived. Such a word or mask is or can be formed in real time either in short intervals between the sampling of X-rays and/or BSE signals at each raster point, or is formed for a given raster point during the time interval during which the data from the next raster point is being collected. Alternatively a series of mask values can be saved until a time interval sufficient for interpretation occurs.

One or more wavelength spectrometers may be used in combination with EDS and formation of a raster or line image by movement of the electron beam. Automatic movement of the sample so that the electron beam can be swept over a new area or line may be practised when practising the present invention.

In FIG. 1 a conventional scanning electron microscope (SEM) 10 is shown, this having a source 12 in use producing a collimated beam 14 of electrons which is directed onto a sample 16 to be analysed. The SEM has deflecting means 18 operable to cause the beam to scan the surface of the sample in a suitable raster pattern such as the series of parallel lines 20 shown. The beam is moved along each line in succession and caused to pause at successive ones of the series of spots 22 in each line. X-rays and backscattered electrons produced at each of the spots pass two detectors 24, 26 respectively from which are produced respective first or X-ray signals and second or BSE signals on respective lines 28, 30. The X-ray or "EDS" detector 24 is an energy dispersive detector of conventional form and produces, for each spot, a time spaced series of X-ray signals of amplitudes which are representative of energies of X-rays generated at that spot pursuant to incidence of the beam thereof. BSE detector 26 may likewise be of conventional form, producing the aforementioned BSE signal therefrom as an analogue signal representative of the intensity of backscattered electrons at the spot upon which the beam 14 is incident. By examining the signals from detectors 24, 26 it is possible to deduce properties such as elemental or phase compositions of the sample 16. More particularly, Table 1 shows examples of numerous mineral phases which are recognizable by examination of peaks in X-ray energy produced by incidence of beam 14 on a spot 22. These peaks are represented by maxima in the numbers or "counts" of the aforementioned X-ray signals from the X-ray detector which are of particular amplitudes. The invention makes use of these counts and "spectrum" counts in a particular way to facilitate analysis of the sample. This is accomplished by using the whole or a sufficient part of the X-ray energy spectrum, and particularly by the use of two or more regions of the spectrum, or combinations of such regions as count values against which to normalize X-ray peak or peaks of a given element(s) in a given phase. Alternatively the number of counts in the peaks may be summed, with or without background subtracted, to obtain a similar useful result. In one version, X-ray count accumulation at a given electron beam dwell point is continued only until the counts for the total spectrum, or a sufficient part of it, or for two or more parts independently, equal preset values. This value, or values, which will usually also include all other X-ray counts due to given elements present in the sample is always higher than the value for a given peak, and is in many cases much higher. Thus normalization always occurs with a statistical accuracy higher than, and often much higher than, that obtained from any given elemental X-ray peak. The time to accumulate the counts for such a peak, with a given expected confidence level, is thus determined by the accumulation of the total spectrum, or a sufficient part of it, and not merely by accumulation of the peak itself, and essentially the same confidence level is achieved whether the peak is there or not.

The counts corresponding to a given element in a given phase will then have a predetermined value (with an estimated standard deviation of the square root of the value) if the electron beam spot is incident on such a given phase or composition. If the beam is incident on some other phase, which does not contain the given element, only background counts, to a specified value, will accumulate in the given channel. The count value in the channel corresponding to the specified element is independent of the time taken to accumulate the spectrum. In real time image formation this means that the beam is only kept at a given image point just long enough to accumulate sufficient spectral counts to define a desired confidence level in the various peaks to be defined in any one of them, and an arbitrary dwell time at each image point need not be used during which either more or fewer counts than are needed are accumulated. For a rough or sloping surface, from which counts are obtained more slowly due to sample-detector aspect or to increased absorption of X-rays within the sample material, automatic accommodation is made, and for multiple detectors, shading of one or more does not affect the outcome. In addition, the background corresponding to the energy window width within which a given X-ray spectral peak from a given phase or composition is sampled, is also normalized with respect to the total spectrum or part thereof, and can thus be precisely defined.

It has been found that independent accumulation of two regions of the X-ray energy spectrum, namely 0.80 to 4.20 KeV, and 4.20 to 20.0 KeV, allowed reproducible X-ray count values, well within the limits required for real time elemental identification by thresholding or by taking ratios, to be obtained from polished sample surfaces lying at angles between 60° tilted towards a detector located at 35° to the horizontal and at up to 35° tilted away from the detector. Other convenient energy ranges can also be used.

The time taken to accumulate the separate regions of the spectrum can vary widely with angle as shown in Table 2, but the counts in a given elemental X-ray channel normalized to the spectral region counts, were nonetheless highly reproducible as can be seen from Table 2. Even for whole, three dimensional, particles with fractured or rough surfaces, where various scattering and absorption effects reduce the X-ray counts in a given peak with respect to spectral or local background, the ratios between X-ray peak counts for pairs of elements in a given phase remain substantially constant.

The cumulation rates in two or more regions of the spectrum may be separately monitored. If such monitoring shows that the required spectral count will not be attained in a specified time, counting for that region of the spectrum, or for the whole spectrum, is discontinued and the beam is moved to the next raster point. This limits the time spent at any one point if no or insufficient X-rays are being produced, or if significant rates of elemental or background counts are produced in one of the normalized regions only. Since the X-ray background count value in a region without peaks is dependent on the average atomic number of the material under the beam producing peaks in other spectral regions and the backscattered electrons signal level is also a function of this average atomic number the BSE signal level can be used to dynamically modify the threshold values at which counting is discontinued.

The value of 4.20 KeV or some value, experimentally adjustable, in the close vicinity, optimizes for example the sulphur/iron count ratio discrimination between compounds such as FeS and $FeS_2$. In general, as shown by the examples in Table 2, use of the specified regions enables consistent ratios to be obtained between X-ray peaks in the region 0.8 to 4.2 KeV and those in the region 4.2 to 20 KeV. Values close to 4.20 KeV also have the advantage of being in the region where scandium $K\alpha$ and $K\beta$ X-rays occur. As this element is rare, there are usually no peaks in this region.

One means of accomplishing the above consists of presettable digital counters following one or more single channel energy windows which accept all or a specified part of the total spectrum and which can be preset to a given value. The signal resulting from this counter when the preset value is reached is used to shut off the accumulation of counts in the various channels receiving X-ray counts corresponding to a given element or group of elements, or to the background in the window region of such a peak, or for any other part of the spectrum which is of interest. This signal, or a sequence of such signals, also triggers the comparison circuits of the digital scan control system, which then proceeds as at the end of any usual or arbitrary beam dwell period.

Notwithstanding the use of peak to spectrum ratio normalization as above-described, it is also possible to use an anti-coincidence peak to spectrum ratio method in which the spectrum or relevant portion of the spectrum does not include the peak or peaks in question. This is achieved by taking the counts accepted for a given peak or set of peaks, cumulating them in each of the counters appropriate to the given element or set of elements, and at the same time, or with a short delay to accommodate the circuit logic, subtract them from the total cumulated spectrum or part thereof, either in the spectrum normalization counter, as above, or in a separate counter. Alternatively, the counts within a peak or peaks can be continually added to the preset value against which the total cumulated spectrum or part thereof is compared. Thus the normalizing spectrum can be made to consist either of total counts in a spectral region, or of those counts in a region not including the peak or peaks of interest, or alternatively of the total counts of all peaks of interest excluding the regions not in the peaks, or of some prechosen combination of regions. This normalization is particularly useful in discriminating different minerals with common elements on the basis of the amount of that element present. For example the ratio of a given peak to the remainder of the spectral region can be taken and this ratio can be again taken as a ratio against the ratio of another peak to the remainder of spectral region in an alternate, or the same part, of the spectrum. For the examples given in Table 2, discrimination of FeS$_2$ and FeS on this basis would give results shown in Table 3.

There is thus produced a 50% differential between the A/B ratios for FeS and FeS$_2$, as compared with a 17% differential for direct S/Fe ratios, and discrimination is accordingly considerably easier.

Figure 2:
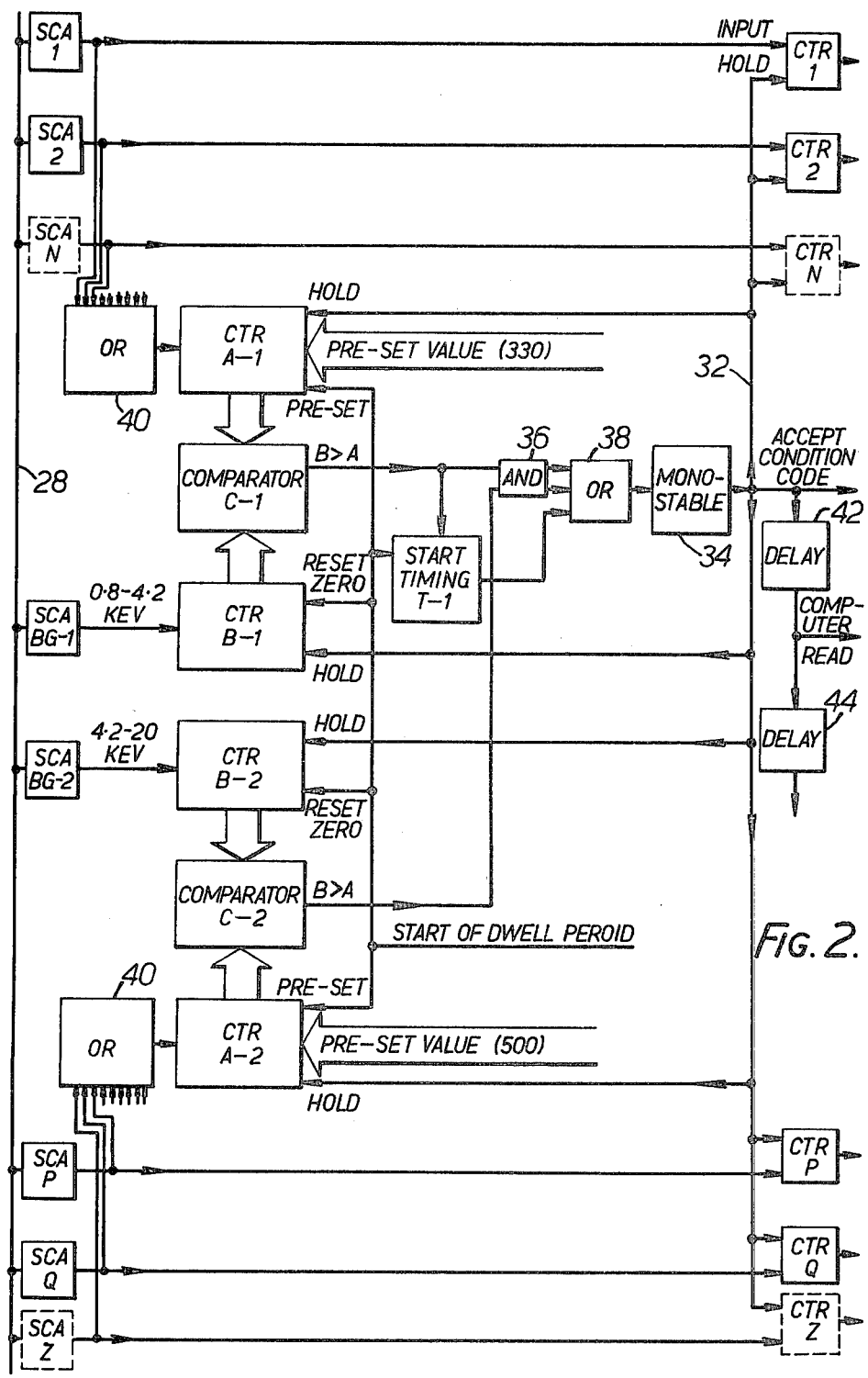
FIG. 2 is a circuit diagram of apparatus useful in analysing X-ray signal information.

A suitable means of implementing the invention is shown in FIG. 2. In FIG. 2 single channel analysers (SCAs) 1–N and P–Z, or their digital equivalents, each have their windows set to allow passage of signals from X-ray detector output line 28 representative of a particular spectral peak, expected when a particular element is irradiated by the SEM electron beam.

Two separate SCAs, BG-1 and BG-2, have their pass windows set much wider. BG-1 accepts pulses, for example in the 0.8 to 4.2 KeV range, and BG-2 in the 4.2 to 20 KeV range. Through these SCAs the total counts occurring in each of the spectral regions are accumulated in counters B-1 and B-2, where they are compared with those in presettable counters A-1 and A-2 by means of comparators C-1 and C-2. In the simplest two-region mode, A-1 and A-2 are preset with given values e.g. 330 and 500. When B-1 has collected 331 counts its comparator sets high and individual counters 1, 2 ... N are prevented from accepting further counts via signals on 'Hold' lines 32. Similarly, and independently of B-1, B-2 collects 501 counts before counters P, Q, ... Z are held at their current contents value. Response of both comparators signals completion of the sequence. If neither B-1 nor B-2 reach the preset value in a pedetermined time, typically 40 or 50 milliseconds, a timer T-1 halts all individual counters.

Termination of the X-ray count collection period by either method causes a signal to appear at "Accept Condition Code", this signal being, generated by a monostable 34 responsive through gates 36, 38 to the conditions of comparators C-1, C-2 and of timer T-1. Appearance of the "Accept Condition Code" signal initiates comparison of the contents of counters 1, 2 ... N and of P, Q ... Z with preset values or may be used in ratio calculations as described later. All counters are then cleared to zero, A-1 and A-2 are preset to 330 and 500, the beam moves to the next spot in the raster and counting is commenced at this point. These operations are effected after delays following appearance of the "Accept Condition Code" signal, the delays being induced by delay circuits 42, 44. If it is desired to compare a given peak or peaks with the remainder of the spectrum in the given spectral region as, for example, counts in the FeKα peak with the remainder of the spectral counts in the 4.2 to 20 KeV region, counter A-2 can be set to 500 prior to counting and, as counts occur in the desired peak, say through SCA-'P', they are added continuously to those in A-2 thus maintaining their difference. The counts in this peak have thus been normalized to those in the spectral region less the peak counts themselves. The peak count value, notionally, corresponds in this case to the ratio P/(S−P) where P stands for the peak counts and S for the total spectral region counts including the desired peak. As in the simpler case, P/S, it is not actually necessary to perform this computation in order to determine if the ratio would fall into a given value range, but merely to inspect the value P contained in counter P. Similarly with counter 1 collecting, 331 counts are preset the 0.8–4.2 KeV region is used to normalize the peaks occurring in this region. By appropriate adjustment of the acceptance ranges for ratio calculations, as described later, a normalized iron to sulphur X-ray count ratio can be obtained by taking the ratio in counts from CTR.P to those from CTR.1 with final results as given in Table 4.

More than one peak at a time can be added to counters A-1 or A-2 by the use of switches, or gates, on the inputs to OR-gates 40 connecting between SCA-1 ... N and A-1 and SCA-P ... -Z and A-2.

In some cases it is sufficient for normalization of counts within peaks, optimization of counting time, and attainment of given confidence levels to feed all counts from 0.8 to 20 KeV into one counter, either B-1 or B-2 or to preset both counters to the same value, in order to normalize the counts within all peaks examined (CTR.1 ... N and CTR.P ... Z) to the total spectrum, or to the total spectrum less the counts in the peaks.

The above methods may be further refined by prior estimation of the peak to background ratio for the actual channel or channel group accepting a given peak, and including a logic divider or other device which reduces, in the ratio of background to peak, the number of counts being subtracted (i.e. those in anti-coincidence) from the spectrum. In this way only the elemental X-ray counts and not the background counts at the same energy are subtracted from the spectrum.

In summary, the above particularly described method provides a method for the normalization of X-ray counts whereby:

(i) a predeterminable background for a peak can be set and obtained;

(ii) a predetermined number of counts can be obtained in the peak (subject to normal random X-ray statistics, i.e. a count of N with a standard deviation of $\pm\sqrt{N}$);

(iii) the time taken to accumulate an image based in whole or part on elemental X-ray counts or combinations of them, can be optimized while at the same time a desired confidence level for compositional identification at each point of the image raster can be achieved;

(iv) the ratios between given peaks in an EDS spectrum of a given phase, or discriminant ratios between X-ray peaks for different phases can be determined and set with a definable confidence level;

(v) all discriminations based on windowing or thresholding or on ratio between different X-ray peaks counts, and all such X-ray identification procedures including full spectral peak stripping by separate software, can be made independent of electron beam current values or drifts, independent of the rate of accumulation of X-ray counts, and independent of the efficiency of a given EDS counter or of the use of more than one such counter even when variations in surface slope prevent one or more of a set of multiple detectors from receiving X-rays;

(vi) a peak to spectrum ratio can be obtained in which the spectrum or spectral region does not necessarily include the peak counts themselves for the element or elements of interest;

(vii) the above properties can be obtained even on strongly sloping surfaces or on the surfaces of particles or fragments, substantially independent of the slope or roughness of such surfaces, and sufficiently independent to allow element or phase identification of materials exposed in such surfaces;

(viii) the above properties can be obtained essentially independently of the nominal take-off angle or angles of the X-ray EDS detector or detectors.

Figure 3:
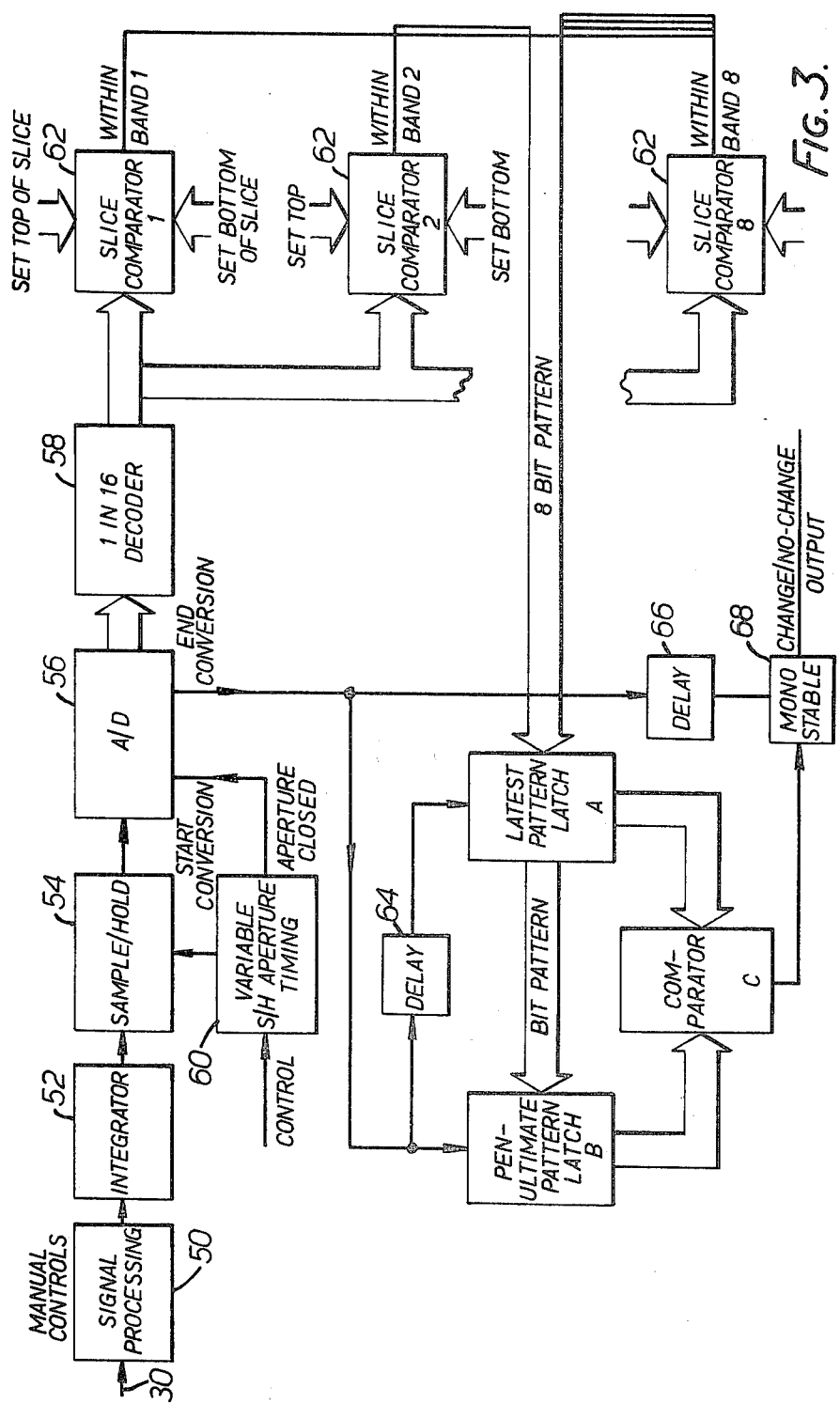
FIG. 3 is a circuit diagram of apparatus useful in processing backscattered electron information.

The BSE signals produced from BSE detector 26 are also useful in analysis of sample 16. These signals can be used for example to build up a "photograph" like image of the surface of the sample. For analysis purposes in accordance with this invention, the BSE signals are preferably sampled at each raster spot and then digitized. More particularly, the signal at each spot is preferably allowed to rise to its full value before being sampled, and then integrated for a specific time period and this integrated value taken as the measure of the BSE signal, this measure then being converted to a precise digital value, e.g. with a resolution as great as that of the signal to noise ratio, its occurrence within a predetermined value band can be used to generate a specific digital response indicating an occurrence within that band. Value bands can extend across any part of the total range, and may be contiguous or overlapping. 8 such bands may be used, with a digital resolution of 1 in 16. A resolution of 1 in 32 or 1 in 64 could equally well be used depending on signal to noise ratio in the analogue signal, which in the present example is 50:1 at mid range (backscatter electron coefficient of 0.3) using a solid state silicon semiconductor detector. Other detectors such as optical scintillator types could also be used. A schematic diagram of the BSE signal processing unit is given in FIG. 3. In FIG. 3 the processed analogue signal, derived from the BSE intensity, is passed through a signal processing circuit 50 and thence passed to an integrator 52 where it is integrated continuously and locked in by a sample/hold circuit 54 at the level attained a preadjusted time after the beam has stopped at its current dwell spot. An analogue/digital converter 56 is connected to S/H circuit 54 and effects analogue/digital conversion some very short time after lock-in and an End of Conversion pulse becomes available when A/D conversion is complete. Operation of the S/H circuit 54 and the converter 56 is effected under control of an adjustable timing circuit 60. The digital value obtained from converter 56 is then true and one of 16 corresponding possible grey levels is set in a decoder 58. If this grey level falls between set limits slice comparators 62 connected to decoder 58 will have corresponding output bits set. Eight slice comparators are shown, combining to define an 8-bit pattern. This current pattern is available to latch 'A'. At the end of A/D conversion the contents of latch 'A' are transferred to latch 'B'. A fixed delay time later set by delay 64, the new current bit pattern is latched into latch 'A'. Comparator 'C' continuously checks latch A against B and if they are different changes its output to a high state. A further delay time later set by delay 66, a monostable 68 is activated producing an extended pulse if latch A is different from B, no pulse if they are the same.

Use of this BSE signal processing in a system which identifies or discriminates phases by their backscatter electron response, avoids a succession of spurious identifications as the signal value rises or falls to a new final value when a new phase is encountered. Also, the degree of confidence of identification is increased by converting an integrated signal rather than an instantaneous or dynamically sampled value. Furthermore, the quality of the visual or photographic image produced by real time display of the sampled and processed image points is more uniform and better discriminated in region of the same or different composition respectively, and the procedure acts to enhance the visual or photographic image obtained from an SEM.

BSE and/or X-ray count information may be used to construct in real time and at high speed a digital word or mask corresponding to a given composition or phase at a given image point or spot, the said digital word containing values 0 or 1 at defined positions to define the presence or absence of a given element on the basis of X-ray events and/or a digital value or bit pattern representing the BSE brightness level. The above-described real time identification of mineral or other phases is by use of BSE brightness levels alone or in combination with X-ray identification. When the latter are not required for any or every compositional identification, the correspondence between each of the chosen BSE value bands to a given mineral or phase may be established by prior EDS identification of the various phases of interest. An example of the simultaneous quantitative evaluation of the phases present in an ore section by means of BSE signals alone and by means of X-ray plus BSE signals is given in Table 5.

The digital word is formed by the combination of digital "yes", "no" responses to a series of events or the encoding or acceptance of digital values from the various analogue or numerical responses available in the system when the irradiating beam is caused to dwell at a given raster point. In particular, the electronic pulses corresponding to a given energy range for a given elemental X-ray detected by an EDS analyser can be fed to a set of parallel analogue discriminators (single channel analysers) each followed by a counter whose contents are compared with a preset value or the occurrence of a digitized value of the pulse value falling into a given range can cause a count pulse to be fed to such a counter. If the preset value is reached during a given dwell or count period, or during a controlled count period as described below, the presence of the element or of a given concentration range of the element, or of more than one concentration range, is accepted and a digital bit is set at 1 in a defined position in the digital buffer. If the element is absent the bit is set at zero. Such 1, 0 digital values may also be derived from X-ray ratios as later described. Use is made in the preset counters or comparison values, of values which just discriminate, at a 99.5% or other convenient confidence level, X-ray peak counts from background counts. A raster display screen may be provided on which the yes/no responses from each or any of the X-ray channels is displayed as a bright dot as the scan proceeds, thus permitting an operator to adjust the preset count level until visual inspection shows him that the response obtained for a given preset count value corresponds to a specific image area known to represent the element or mineral or phase sought.

The digital buffer holding the digital word defining the species composition is also caused to accept a digitally coded value which specifically designates the value band into which the BSE response of the species falls, as described above, with results typified by those in Table 1.

Figure 4:
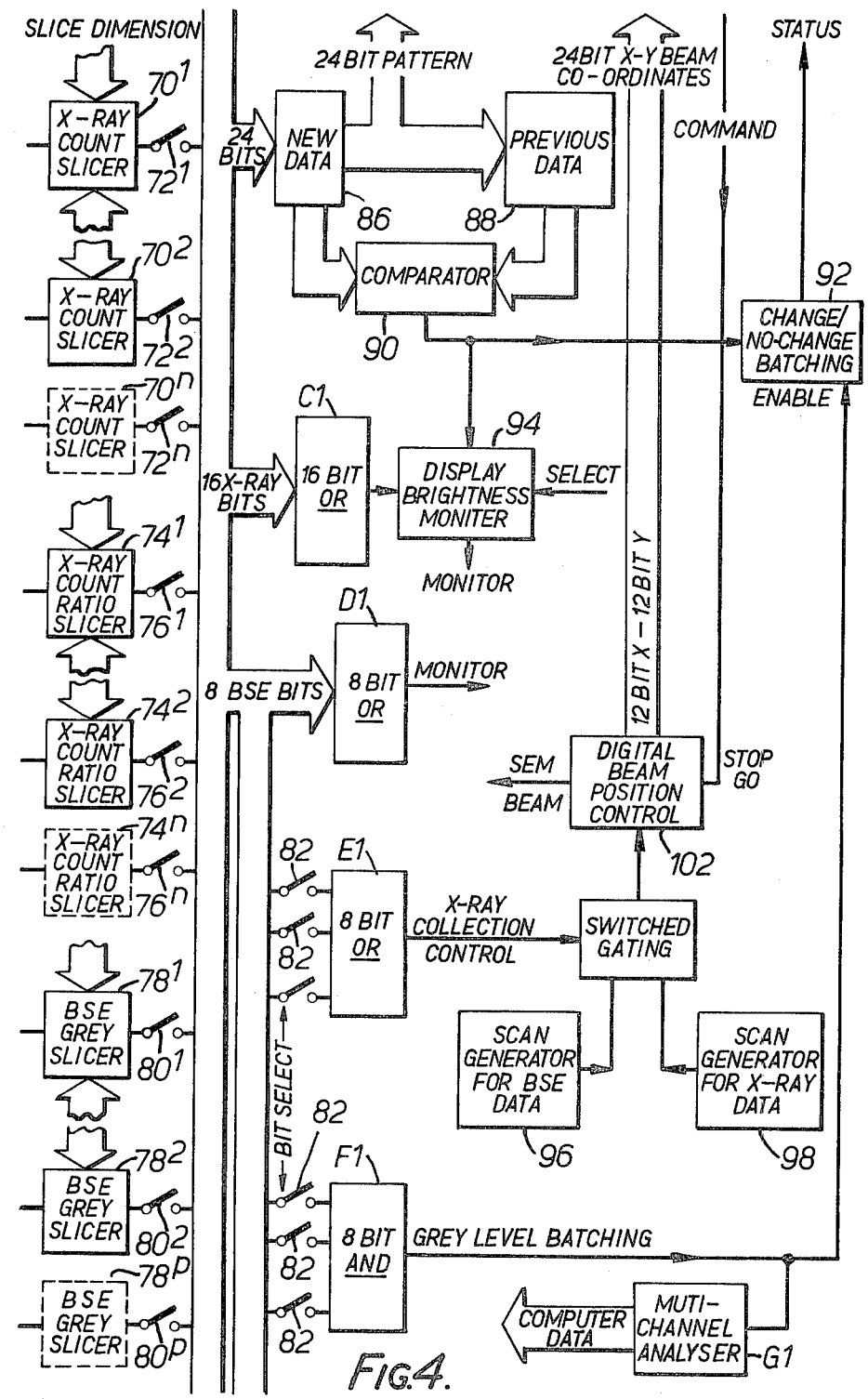
FIG. 4 is a circuit diagram of a system for forming data words or masks from backscattered electron and X-ray count information.

An example of the implementation of the method of the invention, under control of a computer (not shown) is shown in FIG. 4. In FIG. 4, X-ray pulses from the EDS detector are level discriminated in the set of SCAs. SCA-1 ... SCA-N and SCA-P ... SCA-Z previously described. Slicers $70^1$, $70^2$, ... $70^n$ (left of page) accept the SCA outputs and compare the number accumulated in an alloted dwell time with upper and lower limits. If the number lies within these limits an output bit is set by closing an associated switch $72^1, 72^2 \ldots 72^n$ if not the output bit is reset. The accumulated count in certain counters is compared by slicers $74^1, 74^2 \ldots 74^m$ with the value accumulated in others, to produce a ratio of counts between given pairs. This ratio is compared with upper and lower limits and an output bit is set by closure of an associated switch $76^1, 76^2 \ldots 76^m$ if within limits, reset if not. Backscattered electron signal amplitude, a function of the average atomic number of the mineral under the beam, is sliced into 16 grey levels by slicers $78^1, 78^2 \ldots 78^p$. Eight upper and lower limits are set by closure of respective switches $80^1, 80^2 \ldots 80^p$ and if the signal amplitude falls within a defined range an output bit it set if not it is reset.

Before the beam is allowed to proceed to the next spot in the scan raster, the current bit-pattern, derived from X-ray and BSE bits, and represented by 'new data' latch 86 is compared by a comparator 90 with the pattern at the previous spot represented by previous data latch 88 in 'Compare A-B'. A detected change produces an active status condition set in a latch 92. When this condition bit is set the computer responds by reading the X and Y co-ordinates of the raster spot and current pattern, after which the beam scan is restarted.

By switching off all but one X-ray count or ratio slicer output the presence or absence of a single element or mineral may be monitored on a brightness modulated screen, responding to the 16-bit OR-gate, C1 and brightness modulator 94. The screen may optionally be used to display points of change of homogeneous run lengths. Grey level slicers may be monitored on a second screen through gate D1.

If elemental identification by X-rays is not required at all points, such identification, with its longer dwell time, may be limited to areas with a particular grey tone. The dual scan generator system may be switched from X-ray speed and step-interval to BSE speed and interval by entering one or more grey slicer outputs into OR-gate E1, the output of which selects the scan, by gating either a BSE scan generator 96 or an X-ray scan generator 98 through a gate 100 to a control 102 for the beam. In this regard, collection of X-ray data requires longer time intervals than BSE data, so that faster scanning is employed when only BSE data needs to be recorded.

If some changes in grey-tone are not required as computer data the grey level slicer output bits may be batched in AND-gate F1. This forces the active 'Status' to inactive on selected grey levels.

The input to Multi-channel Analyser G1 may be opened on selected batches of grey tones to provide a cumulative spectrum collected on areas of interest. The spectrum may be transferred for analysis and/or verification at the end of each scanned frame or be allowed to accumulate over many frames for an overall spectrum of the whole sample.

A major advantage of the method used is that a minimum dwell time can be selected which minimizes image acquisition time for a given real time reliability in the recognition of given sets of elements and combinations of elements in the sample or specimen.

In the present example the elemental X-ray responses or their ratios are contained in up to 24 bits and the digitized electron or photon responses in a further 8 bits. Other bit combinations can obviously be used.

The comparator 90 permits the digital mask formed at each raster point to be compared with that at the previous point. When these values are the same the scan generator may be arranged to automatically continue without communicating with the computer or memory. When they are different the scan may be halted, the system computer called by a signal from the scan generator and the X and Y co-ordinates and digital mask of the dwell point transferred to the computer. This technique obviates transfer of redundant image points, thus leaving the computer free for other tasks in the transfer intervals, and in particular allows the immediate storage of the image in condensed run-length form in which a succession of image points having the same composition are defined by their first and last positional values only.

The two independently and automatically controllable dwell times provided by generators 96, 98 may typically be of 1 to 1000 microseconds for BSE sampling and of 1 to 1000 milliseconds for X-ray sampling. A very rapid movement of the beam from a given point to the next spatially defined point in the digital raster is also provided, independent of the dwell time or times employed at the point or points. The sweep speed between dwell points is derived from a 10 MHZ or 20 MHZ digital pulse generator driving a digital to analogue converter.

The spatial co-ordinate values and compositional mask of a particular raster spot may be arranged to be not recorded or transferred to any desired memory array until a difference between successive masks is found.

The invention can be adapted for minimizing the amount of data stored and manipulated during image analysis of particles or areas of interest, both simple and complex, within the sample field.

Thus, there may be formed, during raster scanning at high speed, a limited binary or multinary image based usually on BSE signals alone or on BSE signals plus limited X-ray signals, from which the minimum information is extracted necessary to define the minimum and maximum X and Y co-ordinate points of each object or area of interest.

The list of such values is stored, and the scan generator is then addressed with the set or values for one object at a time. The limited area, usually rectangular, enclosing this object is then sampled or scanned in detail using the various aspects of the invention. This limited image data can then at the end of the limited scan for the single object, be treated in the associated computer facility during the scan of the next single object. In this way the computation of image parameters for each individual object can be conducting during the course of the scan of the regions or areas of interest in the total image field, with, in general, the computation for one object occurring while the data for the next is collected.

It is also possible to decode the X-ray and BSE bit pattern to define, as a specified number, the specific mineral, phase or composition at a given raster dwell point, while the data for the next dwell point is being collected. In general, since data transmission to the control computer occurs only when there is a change of composition, there is sufficient time for such decoding.

Acquisition of X-ray signal data may be controlled subject to BSE signal value or values. Any or all of the BSE value ranges (8 in the example of FIG. 4) can be set to allow (or disallow) the collection of X-rays, with the obviation of consequent longer dwell times necessary for "yes-no" X-ray identification for the elements present. For example, if lead sulphide or some substance having a high backscatter electron coefficient is present, the BSE value alone can identify this substance and X-rays need not be collected. Similarly, if an X-ray identification of dense minerals, with high electron backscatter coefficients, but not of silicates or other gangue minerals, with lower BSE coefficients, is required, X-rays are taken when BSE values are above a given level only. This technique allows a considerable saving in time when only specific phases or groups of phases need to be identified by X-rays. The technique also includes thresholding, as used in prior art, in combination with keeping dwell times short when the electron beam is on background, i.e. plastic mount material or low density mounting materials such as carbon or beryllium. In the present invention, fast and slow scanning (short and long dwell times) is not confined to thresholding, but can be applied to any grey level band or combination of bands.

The real time formed digital word or mask containing X-ray 0,1 values for elemental identification together with a digitized value of BSE range or ranges as generated by the system shown in FIG. 4 may be modified by suppressing defined groups of X-ray values or groups of values. For example, some or all X-ray elemental identifications associated with sulphides can be suppressed when the BSE signal brightness indicates silicates. Thus at silicate-sulphide phase boundaries for example, where X-rays due to both species are generated, creating a complex digital mask pattern, the complexity can be greatly reduced by suppression of one group or the other, depending on BSE brightness value.

This suppression can be made subject to analogue BSE signals, with a digital gate, reed relay or other device suppressing transmission of the specified X-ray bits, or to the digitized value or value range of the BSE signal. In this latter case digital logic units or software can be used to suppress unwanted X-ray bits.

This procedure drastically reduces the complexity of interpreting digital mask patterns, especially those arising at phase boundaries or other regions of ambiguity, and typically any or all of 12 elements can be recognized simultaneously, corresponding for example to up to 30 defined minerals. Thus, prima facie a matrix of $2^n$, where n is the number of elements, has to be decoded. By use of the present method, the problem is typically reduced to the decoding, for $n=12$, or two matrices each of only $2^6$, a total decrease in magnitude of $2^5$.

Figure 5:
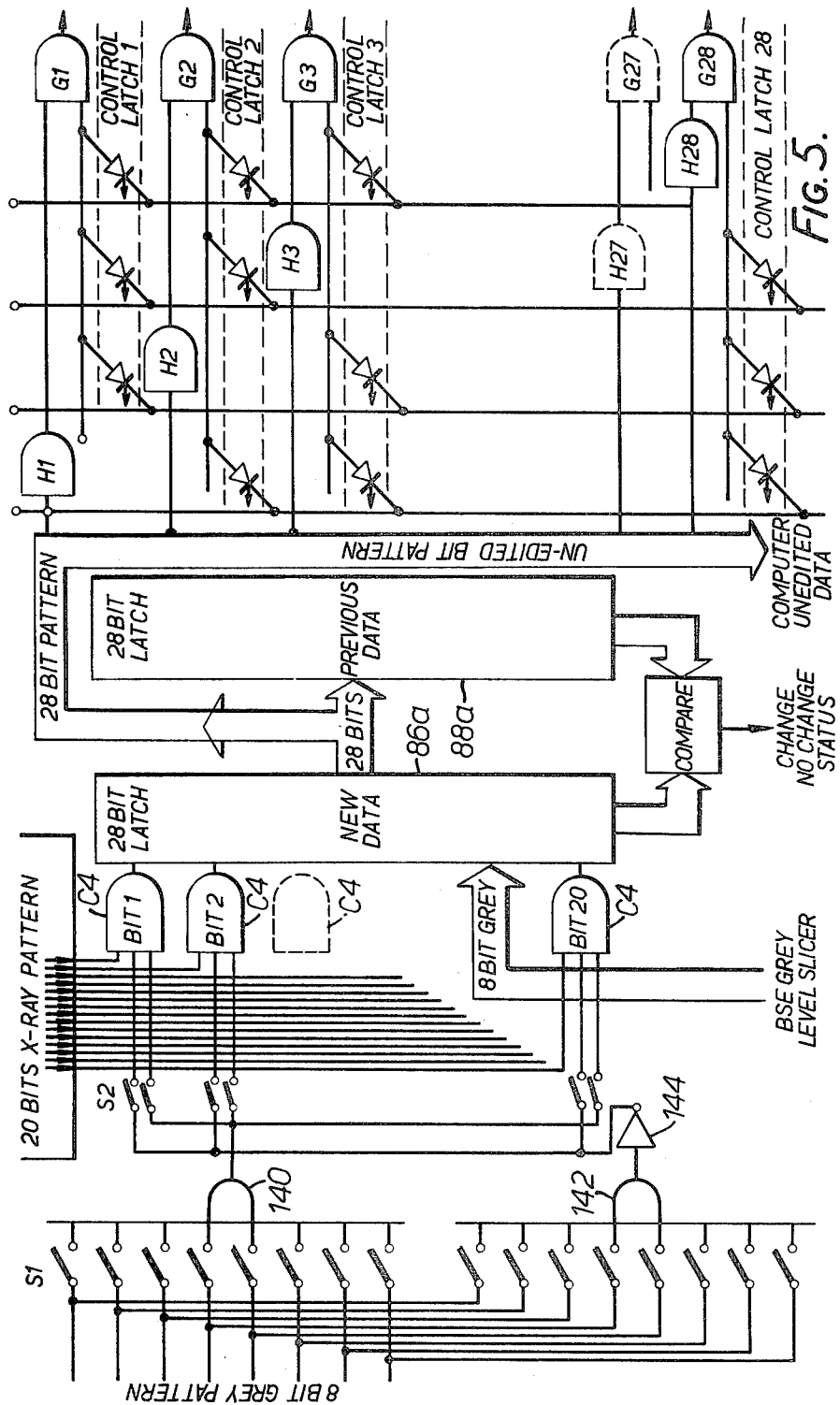
FIG. 5 is a circuit diagram of a modification of the system of FIG. 4 adapted for inhibition of storage of full word or mask data in accordance with grey levels of backscattered electrons.

Table 1 previously referred to is an example of a set of mineral phases which can be simultaneously identified during modal or image analysis of a sample from a typical complex ore, in which at least 20 different minerals were present. Such an analysis can be facilitated by using a threshold value and two brightness ranges for BSE signals, together, say, with 12 X-ray channels. A modification for this purpose to the system of FIG. 4 is shown in FIG. 5. Here, the latches 86a, 88a and comparator 90a take the place of the latches 86, 88 and comparator 90 of FIG. 4. The input of X-ray and BSE data is effected in a slightly different fashion, however. Thus, in FIG. 5 8 BSE grey levels, observed at a particular point in the scanned raster, are made available to two 8-input AND-gates 140, 142. By means of switches S.1 any or all of the grey levels may be made to contribute to the decision whether the outputs of gates 140 and 142 are set. A 20 bit X-ray pattern, derived from count and/or X-ray ratio thresholds or windows as previously described is accepted, through gates C4, as new data only if the correct grey level pattern is present at the inputs to gate 140. The output of gate 142 is inverted by an inverter 144 before entry into the X-ray bit selection gates C4 and therefore X-ray data is accepted as new data only if a particular grey level pattern into B is not present. Switches S.2 determine whether an X-ray bit is to be made subject to any grey level condition being present or not present. Once accepted as new data the total pattern in the 'new data' latch 86a is compared with the data held in latch 88a which was valid at the previous dwell point in the scanned raster and, if different, causes a change in 'Status' which indicates to the computer the need to read the pattern with its X and Y coordinates.

The total bit pattern, derived from X-rays and BSE signal conditions, is also passed on to a cross-bar arrangement consisting of a matrix of gates H1 . . . H28 . . . . In this cross-bar each bit of the bit pattern is available to all other bits as a conditional inhibit level. It is thereby possible to remove a particular bit from the edited output pattern right side of diagram, if a selected conditional pattern is formed by the remaining bits. The information which determines what specific pattern will disable a given bit is entered into control latches G1 . . . G28 from information stored in the control computer library.

X-ray generation by an electron beam occurs in a region up to a few microns in diameter. Thus, within this distance from phase boundaries, X-rays from each phase are obtained. Use of BSE brightness differences between different phases allows the phase boundary to be located with the resolution of BSE SIGNALS, typically 0.1 microns, while selected X-rays, or groups of X-rays, corresponding to the BSE values on either side of the boundary are used to define the compositions. X-rays corresponding to the alternate BSE value are ingored, and the advantages of limited data decoding are thus obtained.

This procedure also improves drastically the definition of phase or particle boundary location in plastic or epoxy mounts where the phase material dips obliquely below the plastic surface. BSE signals define the plastic or epoxy, even though X-rays are being generated by more deeply penetrating electrons and would otherwise falsely indicate the location of a boundary on the true plane of polish or sectioning.

Previous reference has been made to the real time formation of X-ray count ratios which enable short-dwell times and low total number of accumulated counts to discriminate phases containing common elements, e.g., FeS, and $FeS_2$, or $CuFeS_2$ and $Cu_5FeS_4$. The result of the ratio computation is a digital 1 or 0 corresponding to a ratio value falling within, or not within, a defined range of values, or above or below a given value. This result is recorded as a 1 or 0 bit in the digital mask defining the species composition at a given raster point. The occurrences of such bits, and their correspondence with defined regions of the image, can be displayed on a CRT or storage oscilloscope screen for operator verification, and to allow adjustment of the correct ratio settings.

The level of confidence obtained using this invention is unexpectedly much higher than is obtainable by simple thresholding of a series of acceptance levels for a given X-ray peak. For example, in distinguishing the phases FeS and $FeS_2$, a common and difficult problem in quantifying mineral species, a 99% correct recognition of either phase was obtained with a total number of counts for each of Fe and S of only 100 to 200 at each raster point. At these counts values, with the random statistics governing X-ray production, simple windowing of count values defined in a given case as N, is subject to a standard deviation of $\sqrt{N}$ or a variation of N, and confidence levels for discrimination by thresholding on a given peak were considerably lower than those obtained from ratio values.

This ratio procedure also allows the discrimination of significant amounts of one element in the presence of interfering X-ray peaks of another. For example, the $K\alpha$ X-ray peak of cobalt coincides with the $K\beta$ peak of iron, and the presence of moderate amounts of cobalt is normally difficult to discriminate against the iron $K\beta$ value when low total counts and simple windowing are used. By taking the ratio of the counts in cobalt $K\alpha$ peak position, with or without correction for background, against the counts in the iron $K\beta$ position, the occurrence of significant cobalt in the mineral or phase, even in the presence of some iron, can be readily distinguished in real time, i.e. during the image scan, and with short dwell times. With the EDS system used in the example, dwell times of 20 to 30 msec were sufficient. For discrimination of iron $K\beta$ from cobalt $K\alpha$, especially in the presence of unknown amounts of iron in a cobalt phase, or for overlapping X-ray spectral lines generally, it is generally necessary to accumulate sufficient counts for spectral peak stripping or for peak height comparisons using software mathematical techniques and requiring times of the order of 1 second, i.e. 1 to 2 orders of magnitude greater than are necessary with the present invention.

Figure 6:
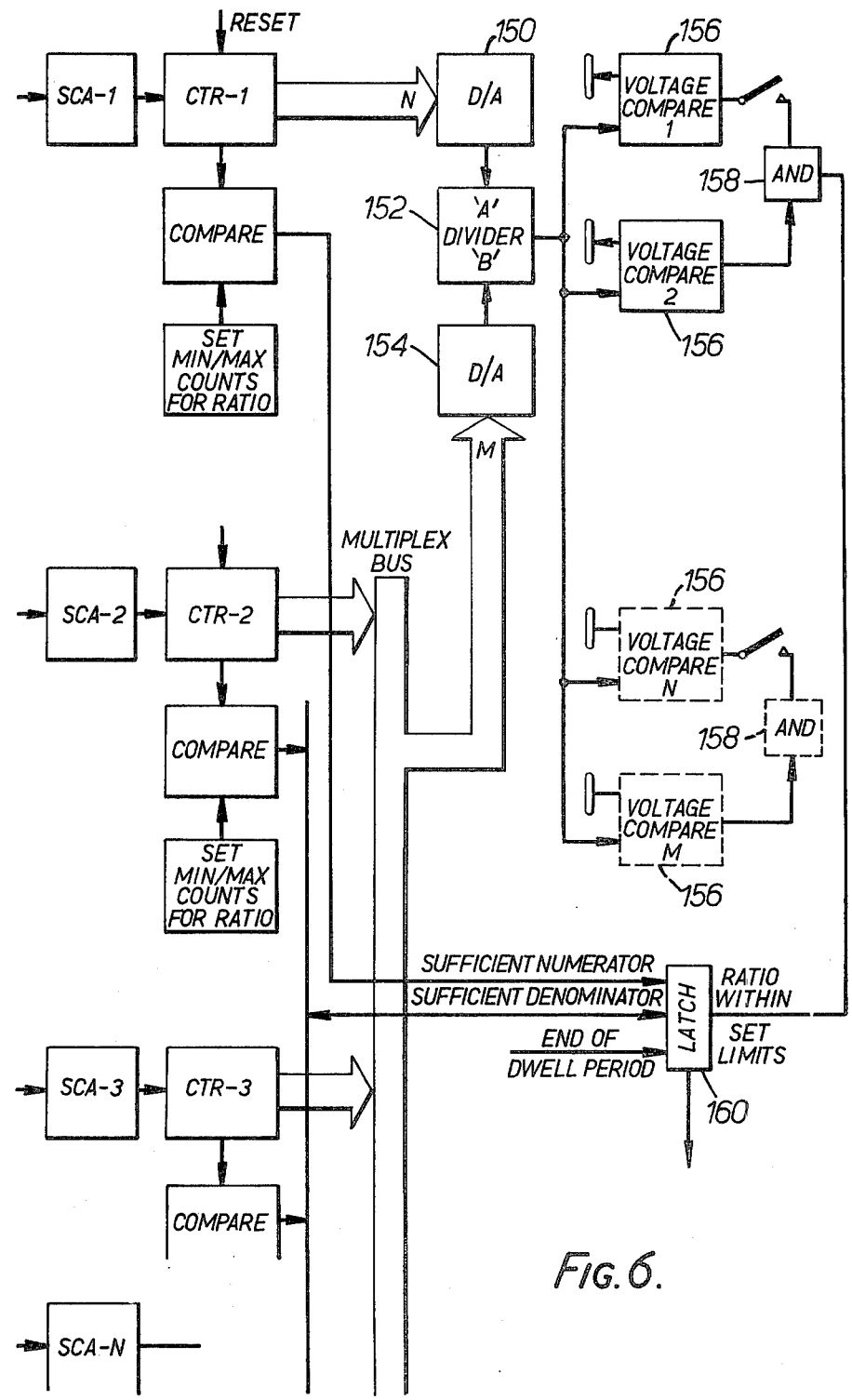
FIG. 6 is a diagram of a system for determining ratios of X-ray signals.

In FIG. 6, single channel analysers SCA-1, SCA-2 . . . SCA-N select X-ray or EDS pulses corresponding in energy to a particular respective element. The pulses from analysers SCA-1 . . . SCA-N are counted in associated counters CTR-1 . . . CTR-N during the alloted dwell time. The count from counter CTR-1 is entered, as a continually changing number N, into a digital-analogue converter 150. Digital-analogue converter output is a voltage level rising with an increase in counts. This voltage is supplied to an analogue voltage divider 152 as input 'A'. A second input 'B' to divider 152 is a similarly derived voltage, the level of which is proportional to the count in one other particular counter CTR-2 . . . CTR-N and corresponding SCA output, chosen by a multiplexed arrangement, as the denominator input M to a second digital-analogue converter 154.

The divider output A/B is a voltage level which is applied to several comparators 156 arranged in pairs. One comparator 156 of each pair is a 'lower level' comparator and the other is an 'upper level' comparator. The outputs of each such pair are connected to a respective AND gate 158. Lower level comparators 156 set an output bit when the divider voltage, i.e. the ratio N/M, is greater than the level set on a 10-turn dial, the upper level comparators set when the ratio is less than that set on a second 10-turn dial.

Combinations of the described pairs of comparators 156 provide windows which set output bits via latches such as the latch 160 shown when a ratio falls within one of these windows. To avoid acceptance of bits set when the denominator is zero, the computer bits are made subject to a sufficient count being present in both numerator and denominator.

It is possible to use fewer, or even only one, digital to analogue converters prior to the ratio comparison and to multiplex in, by rapid switching of counter addresses, a sequence of pairs of numbers to be ratioed. Such procedures can still be accomplished within times short compared with X-ray dwell times, e.g. 10 microseconds per number pair, as compared with 10–40 milliseconds for X-ray dwell times, and thus are still performable in real time, during the progress of an image scan. Alternatively such comparisons can be made on temporarily stored spectra or spectral regions, as either at the end of each dwell period or during the dwell period during which data for the next raster point is being collected.

Quantitative mapping of three-dimensional particles or fragments, especially those containing multiple phases which must be discriminated, cannot normally be performed. Portions of a sloping or rough surface remain shadowed with respect to a single EDS or other X-ray detector 24, and the use of more than one X-ray detector 24 or BSE detector 26 to obtain views of different faces or shapes of the rough surface or particle is included in the invention.

Typically, spheres of a given material such as polystyrene, glass or steel viewed with an overhead detector show shadowed rims in the resulting image, and the BSE signals in particular collected over the upper hemisphere of such objects are not uniform.

It is therefore preferred to use an array of BSE detectors such that the combined signals from the set of detectors gives a closely uniform response (with 1% to 2% variation for example) over the whole of the upper hemisphere of a given spherical object. The results in an example are equivalent for objects in the size range of microns to a few millimeters. The image of such an object can be made to appear as a completely uniform while or grey disk against a background of darker grey or black. For non-spherical or rougher surfaces the degree of variation in the BSE signal as a result of such topography for any given species or phase composition is greatly reduced, and BSE discrimination of different phases on particles, fragments or rough surfaces can still be made.

Figure 7:
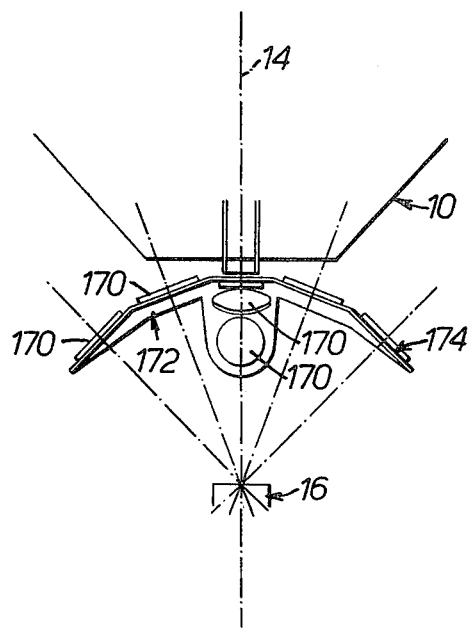
FIG. 7 is a partly diagrammatic side view of a backscattered electron detector array useful in the invention.

FIG. 7 shows such an array consisting of eight Schottky Diode photodetectors 170 (of which only six are visible) of 1 $cm^2$ active area, mounted in pairs at 45° and $67\frac{1}{2}$° to the horizontal, one pair in each horizontal quadrant. Thus, the photodetectors are carried by a cross-shaped metal bracket 172 apertured to receive the photodetectors therebehind. The photodetectors are insulated from the frame by mica washers 174. A separate amplifier (not shown) is connected to each detector, and after gain adjustment, the outputs from the eight amplifiers are summed. The output each amplifies can also be separately converted to a digital value and this transmitted to the control computer. By extension of the procedures described in J. Lebiedzik et al. Scanning Electron Microscopy/1979 II pp. 61–66, "Use of microtopography in the SEM for analysing fracture surfaces", an estimate of the slope of any portion of the surface may then be found, rather than the slope in one direction only. Normally, the detector array is characterized by an approximately axially symmetrical disposition of the detectors, and the placing of each detector so that its face is approximately normal to the point of impingement of the electron beam at the horizontal plane representing the specimen surface.

The techniques of the invention permit obtaining an integrated estimate of the total concentrations of all elements present in the set of particles, ore section, or any other materials comprising the specimen. This is accomplished by opening the input to a multi-channel analyser, analogue-digital converter coupled with addressable memory, or other such device or arrangement, only during the periods when X-rays are being collected for identification of the composition of appropriate raster points in the sampled image field. In this way an X-ray energy spectrum is built up which represents the sum of the elemental concentrations at the points in the image or sample field which have actually been sampled.

This spectrum can then be deconvoluted by known or available peak stripping procedures to provide an overall elemental composition. Such information is of value in its own right, but is especially and additionally valuable in checking and normalizing the elemental composition of the sample as inferred from the proportions of the various minerals or phases identified by the image analysis procedures complementary to the image acquisition procedures described herein. Such inferred values depend on assumed or known compositions and densities for all of the minerals present or identified, and are often subject to systematic errors.

TABLE I
EXAMPLE OF A COMPLEX PHASE ASSEMBLAGE IN WHICH ALL PHASES ARE RECOGNIZED DURING A SINGLE SCAN

| No.[a] | Mineral Phase | Nominal Composition | 1.74 | 2.02 | 2.31 | 2.99 | 3.31 | 3.69 | 4.51 | 5.90 | 6.40 | 8.04 | 8.63 | 10.55 |
|---|---|---|---|---|---|---|---|---|---|---|---|---|---|---|
| | | | | | | | | EDS X-ray peak centre[b], KeV — Element Detected | | | | | | |
| 1 | Galena | PbS | — | — | S | — | — | — | — | — | — | — | — | Pb(Lα) |
| 2 | Sphalerite | ZnS | — | — | S | — | — | — | — | — | — | — | Zn | — |
| 3 | Pyrite | $FeS_2$ | — | — | S | — | — | — | — | — | Fe | — | — | — |
| 4 | Pyrrhotite | FeS | — | — | S | — | — | — | — | — | Fe | — | — | — |
| 5 | Chalcopyrite | $CuFeS_2$ | — | — | S | — | — | — | — | — | Fe | Cu | — | — |
| 6 | Tetrahedrite | $Cu_{12}Sb_4S_{13}$ | — | — | S | — | — | Sb(Lα,β) | — | — | — | Cu | — | — |
| 7 | Freibergite | $Cu_8Ag_4Sb_4S_{13}$ | — | — | S | Ag (Lα) | — | Sb(Lα,β) | — | — | — | Cu | — | — |
| 8 | Bournonite | $CuSbPbS_3$ | — | — | S | — | — | Sb(Lα,β) | — | — | — | Cu | — | — |
| 9 | Arsenopyrite | FeAsS | — | — | S | — | — | — | — | — | Fe | — | — | As(Kα) |
| 10 | Hematite; Magnetite | $Fe_2O_3; Fe_3O_4$ | — | — | — | — | — | — | — | — | Fe | — | — | — |
| 11 | Quartz | $SiO_2$ | $Si(1)^d$ | — | — | — | — | — | — | — | — | — | — | — |
| 12 | Albite | $NaAlSi_3O_8$ | $Si(2)^d$ | — | — | — | — | — | — | — | — | — | — | — |
| 13 | Calcite | $CaF_2$ | — | — | — | — | — | Ca | — | — | — | — | — | — |
| 14 | Manganiferous | $(Ca,Mn,Fe)CO_3$ | — | — | — | — | — | Ca | — | Mn | Fe | — | — | — |
| 15 | Rutile | $TiO_2$ | — | — | — | — | — | — | Ti | — | — | — | — | — |
| 16 | Ilmenite | $FeTiO_3$ | — | — | — | — | — | — | Ti | — | Fe | — | — | — |
| 17 | Barytes | $BaSO_4$ | — | — | S | — | — | — | Ba (Lα) | — | — | — | — | — |
| 18 | Muscovite | $KAl_3Si_3O_{10}(OH)_2$ | Si | — | — | — | K | — | — | — | — | — | — | — |
| 19 | Chlorite | $(Mg,Al,Fe)_3(SiAl)_2O_5(OH)_4$ | Si | — | — | — | — | — | — | — | Fe | — | — | — |
| 20 | Sphene | $CaSiTiO_4$ | Si | — | — | — | — | Ca | Ti | — | — | — | — | — |
| 21 | Apatite | $Ca_5(PO_4)_3F$ | — | P | — | — | — | Ca | — | — | — | — | — | — |

[a]Phases 1 to 10 have BSE coefficients greater than 0.15, and are grouped on that basis
[b]All X-ray peaks are Kα lines unless otherwise indicated. A band approximately 0.2 KeV wide is centered at each peak position for acceptance of X-rays in the peak.
[c]Pyrite and pyrrhotite are distinguished by S/Fe count ratio.
[d]Two independent present levels discriminate the amount of Si in mineral 11, Si(1), and mineral 12, Si(2) or the method of Section 9 are used.

TABLE 2
POLISHED SECTION EDS SPECTRA NORMALIZED IN TWO PARTS

Region A: 0.8–4.2 KeV, 333 counts
Region B: 4.2–20.0 KeV, 500 counts

| Phase | Tilt | Element or Region | Count Peak + BGD | BGD | Time msecs | 3 E.S.d limits | Sulphur/Metal count ratio* |
|---|---|---|---|---|---|---|---|
| $FeS_2$ pyrite | 0° | S | 227 | 13 | 15 | 181/24 | 1.07 |
| | | Fe | 212 | 19 | 18 | 170/32 | |
| | 35° | S | 231 | 9 | 40 | 185/18 | 1.04 |
| | | Fe | 222 | 11 | 34 | 177/21 | |
| | 37° | S | 225 | 10 | 141 | 180/19 | 1.05 |
| | | Fe | 214 | 12 | 42 | 171/23 | |
| $Fe_xS$ pyrrhotite | 0° | S | 205 | 15 | 17 | 163/27 | 0.91 |
| | | Fe | 225 | 12 | 16 | 180/23 | |
| | 30° | S | 211 | 13 | 33 | 167/24 | 0.89 |
| | | Fe | 237 | 11 | 24 | 191/21 | |
| | 37° | S | 212 | 12 | 40 | 168/23 | 0.87 |
| | | Fe | 243 | 11 | 26 | 197/21 | |
| Sphalerite | 0° | S | 169 | 15 | 15 | 130/27 | 0.99 |
| | | Zn | 171 | 12 | 18 | 132/23 | |
| | | Fe | 57 | 15 | 18 | 34/27 | |
| | 35° | S | 177 | 22 | 27 | 137/36 | 1.00 |
| | | Zn | 177 | 9 | 21 | 137/18 | |
| | | Fe | 47 | 13 | 21 | 26/24 | |
| Galena | 0° | Pb | 56 | 14 | 15 | 34/25 12(A) | |
| | 35° | Pb | 63 | 14 | 18 | 39/25 18(A) | |
| Chalcopyrite $CuFeS_2$ | 0° | S | 202 | 15 | 14 | 160/27 | 2.04 |
| | | Cu | 99 | 11 | 16 | 69/21 | |

TABLE 2-continued
POLISHED SECTION EDS SPECTRA NORMALIZED IN TWO PARTS

Region A: 0.8–4.2 KeV, 333 counts
Region B: 4.2–20.0 KeV, 500 counts

| Phase | Tilt | Element or Region | Count Peak + BGD | BGD | Time msecs | 3 E.S.d limits | Sulphur/ Metal count ratio* |
|---|---|---|---|---|---|---|---|
| | | Fe | 150 | 15 | 16 | 113/27 | |
| | 35° | S | 204 | 14 | 39 | 162/25 | 2.02 |
| | | Cu | 101 | 8 | 26 | 71/17 | |
| | | Fe | 153 | 11 | 26 | 116/21 | |
| Bornite | 0° | S | 176 | 19 | 17 | 136/32 | 1.00 |
| $Cu_5FeS_4$ | | Cu | 176 | 9 | 16 | 136/18 | |
| | | Fe | 65 | 15 | 16 | 41/27 | |
| | 35° | S | 170 | 20 | 47 | 131/33 | 0.91 |
| | | Cu | 187 | 9 | 24 | 146/18 | |
| | | Fe | 63 | 12 | 24 | 39/23 | |
| #Covellite | 0° | S | 186 | 16 | 16 | | ~1.0 |
| CuS | | Cu | 190 | 12 | 16 | | |
| Chalcocite | 0° | S | 145 | 20 | 17 | 108/33 | 0.65 |
| $Cu_2S$ | | Cu | 223 | 10 | 15 | 175/19 | |
| | 35° | S | 144 | 21 | 34 | 108/34 | 0.62 |
| | | Cu | 233 | 9 | 15 | 187/18 | |
| Biotite | 0° | Si | 135 | 14 | 16 | 100/25 | 0.99 |
| | | K | 71 | 13 | 16 | 46/24 | |
| | | Fe | 136 | 20 | 46 | | |
| | 35° | Si | 147 | 13 | 39 | 110/24 | 1.07 |
| | | K | 94 | 15 | 39 | 65/27 | |
| | | Fe | 138 | 18 | 74 | 102/31 | |
| Cassiterite | 0° | Sn | 251 | 27 | 8 | 204/43 | |
| | | (≈K) | 128 | 14 | 8 | 94/25 | |
| | | (≈Ca) | 129 | 14 | 8 | 95/25 | |
| | | Region B | | | 25(B) | | |
| | 35° | Sn | 267 | 21 | 13 | 218/34 | |
| | | Region B | | | 34(B) | | |
| Rhodonite | 0° | Si | 173 | 17 | 19 | 134/29 | 0.89 |
| | | Ca | 55 | 15 | 19 | 33/27 | |
| | | Mn | 195 | 14 | 23 | 153/25 | |
| | | Fe + Mnβ | 85 | 12 | 23 | 57/23 | |
| | 35° | Si | 148 | 16 | 36 | 111/28 | 0.72 |
| | | Ca | 75 | 18 | 36 | 49/31 | |
| | | Mn | 205 | 12 | 26 | 162/23 | |
| | | Fe + Mnβ | 88 | 11 | 26 | 60/21 | |
| Hematite | 0° | Fe | 281 | 9 | 15 | 231/18 | |
| | | Region A | | | 44(A) | | |
| | 35° | Fe | 288 | 8 | 16 | 237/17 | |
| | | Region A | | | 73(A) | | |
| Freibergite | 0° | S | 108 | 20 | 10 | 76/33 | 1.4 |
| | | Ag | 76 | 15 | 10 | 50/27 | |
| | | Sb | 50 | 15 | 10 | 29/27 | |
| | | Region B | | | 20(B) | | |
| | 35° | S | 88 | 20 | 16 | 60/33 | |
| | | Ag | 88 | 15 | 16 | 60/27 | |
| | | Sb | 54 | 15 | 16 | 32/27 | |
| | | Region B | | | 26(B) | | |
| $AlPO_4$ | 0° | Al | 126 | 12 | 13 | 92/23 | 0.89 |
| | | P | 141 | 12 | 13 | 105/23 | |
| | | Region B | | | 83(B) | | |
| | 35° | Al | 120 | 13 | 28 | 87/24 | 0.86 |
| | | P | 142 | 13 | 28 | 106/24 | |
| | | Region B | | | 92(B) | | |
| Quartz | 0° | Si | 261 | 9 | 10 | 213/18 | |
| | | Region B | | | 44(B) | | |
| | 35° | Si | 261 | 8 | 45 | 213/17 | |
| | | Region B | | | 99(B) | | |
| Dolomite | 0° | Ca | 203 | 20 | 10 | 161/33 | |
| | | Region B | | | 39(B) | | |
| | 37° | Ca | 230 | 19 | 45 | 185/32 | |
| | | Region B | | | 56(B) | | |

Count values for covellite are estimated.
*or count ratio for dominant two elements.

TABLE 3

| | $FeS_2$ | FeS |
|---|---|---|
| S peak | 227 | 205 |
| Remainder of region A | 106 | 126 |
| Ratio A | 2.14 | 1.63 |
| Fe peak | 212 | 225 |
| Remainder of region B | 288 | 275 |
| Ratio B | 0.74 | 0.82 |
| Ratio A/Ratio B | 2.91 | 1.99 |
| Direct S/Fe ratio | 1.07 | 0.91 |

TABLE 4

EDS SPECTRA FROM A PYRRHOTITE PARTICLE, NORMALIZED IN TWO PARTS

Region A: 0.8–4.2 KeV  333 counts
Region B: 4.2–20.0 KeV  500 counts

| Sample and position | | Element | Counts Peak & BGD | Time msecs | Sulphur/metal count ratio |
|---|---|---|---|---|---|
| Particle | Polished Section | S | 205 | 17 | 0.91 |
| | | Fe | 225 | | |
| | Sloping to detector | S | 204 | 16 | 0.90 |
| | | Fe | 226 | | |
| | Top | S | 197 | 38 | 0.87 |
| | | Fe | 226 | | |
| | Top | S | 184 | 44 | 0.92 |
| | | Fe | 201 | | |
| | Far right | S | 106 | 63 | 0.89 |
| | | Fe | 119 | | |
| | Far left | S | 85 | 144 | 0.81 |
| | | Fe | 95 | | |

TABLE 5

LINE-SCAN MODAL ANALYSIS, POLISHED LEAD-ZINC ORE
Single frame 1.2 × 0.9 mm, 25 lines, 35 microns apart, 1.2 micron point separation, 29 mm total traverse.

| | Pbs | ZnS | Freibergite[a] | FeS | FeS$_2$ | Quartz | Dolomite | Potassium mica | Apatite | Unidentified | Total non Sulphides |
|---|---|---|---|---|---|---|---|---|---|---|---|
| | | | | VOLUME PERCENT | | | | | | | |
| BSE only | 25.6 | 60.4 | 2.1 | 6.9[b] | —[c] | — | — | — | — | — | 5.0 |
| X-ray + BSE | 25.1 | 60.4 | 1.5 | 6.6 | 0.3 | 0.0 | 0.07 | 3.7 | 0.03 | 1.4 | 5.2 |
| | | | | MEAN INTERCEPT LENGTH, microns | | | | | | | |
| BSE only | 24.0 | 43.7 | 10.6 | 28.5 | — | — | — | — | — | — | 9.6 |
| X-ray + BSE | 22.3 | 42.3 | 13.2 | 24.6 | 3.4 | 0.0 | 5.2 | 10.2 | 4.6 | 4.8 | — |

[a]$Cu_6Ag_4(Zn,Fe)_2Sb_4S_{13}$
[b]FeS and FeS$_2$ combined
[c]Not determined

We claim:

1. A method of analysis in which a beam of energy is caused to fall on a spot on the surface of a sample to be analysed and X-rays then generated at the spot are detected by one or more detectors to produce first signals representative of the energies of detected X-rays; comprising making a first count of the number of said first signals each representative of an energy within a relatively broad range of such energies and making a second count of the number of said first signals each representative of an energy in an associated relatively narrow range of energies about one particular energy wherein information relating to the relative proportion of a particular chemical element, characterized by production of X-rays of said particular energy, is obtained in the form of a normalized ratio of said second count to said first count, said normalized ratio being represented by the value of said second count when said first count reaches a predetermined value.

2. A method as claimed in claim 1 in which an additional second count is made, each said second count being a count of the number of said first signals representing the energy in a respective separate relatively narrow range of energies about said particular energy, the particular energy for each second count being different, whereby the assumed value for each second count represents a separate normalized ratio.

3. A method as claimed in claim 2 wherein said first count includes at least one of said second counts.

4. A method as claimed in claim 2 wherein said first count is exclusive of said second counts.

5. A method as claimed in claim 3 wherein at least one said relatively narrow range of energies falls within said relatively broad range of energies whereby the respective assumed value of said second count for said first signals falling within that relatively narrow range of energies constitutes a normalized ratio of peak energy to total energy for the spectrum of energies represented by said relatively broad range.

6. A method as claimed in claim 3 wherein an additional first count is also made, said relatively broad range of energies for each of said first counts being different.

7. A method as claimed in claim 6 wherein the particular energy or associated relatively narrow range of energies for which said first signals are counted to make said second count is arranged to fall within the relatively broad range of energies for which said first signals are counted to form a respective first count, and the particular energy or associated relatively narrow range of energies for which said first signals are counted to make said additional second count is arranged to fall within the relatively broad range of energies for which said first signals are counted to form said additional first count.

8. A method as claimed in claim 7 wherein the said assumed value for said second count and for said additional second count are those reached at different predetermined values for each second count.

9. A method as claimed in claim 8 wherein said relatively broad ranges of energies at least substantially co-join to form an extended spectrum of such energies.

10. A method as claimed in claim 9 wherein there are two of said relatively broad ranges of energies with one extending from substantially 0.8 to 4.2 KeV and the other extending from substantially 4.2 KeV to 20 KeV.

11. A method as claimed in claim 2 wherein at least one ratio of said second counts is also generated.

12. A method as claimed in claim 1 including detecting backscattered electrons generated at said spot by action of said beam thereon and generating a second signal representative of the intensity of said backscattered electrons.

13. A method as claimed in claim 12 wherein said second signal is generated by integrating an output signal from a detector of said backscattered electrons, said beam being caused to fall on said spot for a predetermined time before said integrating.

14. A method as claimed in claim 1 including the step of constructing an information signal from said second count, said information signal containing information as to the analysis of said sample.

15. A method as claimed in claim 14 wherein said information signal is in the form of a digital word.

16. A method as claimed in claim 14 wherein said beam is caused to fall successively on numerous spots defining an image raster over the surface of said sample, for generating a plurality of information signals, one for at least each selected one of a set of selected spots, with at least the first information signal being stored.

17. A method as claimed in claim 16 wherein, for two successive said spots, corresponding information signals are compared, the first of these information signals being stored and the second of these information signals being stored at least in full form only if it differs from the first.

18. A method as claimed in claim 16 wherein second signals generated for first and second successive spots are compared and the information signal corresponding to the second of such successive spots is abridged by not generating or only partly generating second counts for that spot if the second signals for the first and second successive spots are substantially the same relative to the other.

19. A method as claimed in claim 18 wherein corresponding second counts for numerous spots are accumulated to give an average compositional indication for said sample over an area thereof represented by said spots.

20. A method as claimed in claim 18 wherein a first set of said information signals is first generated and from this first set are generated maximum and minimum orthogonal co-ordinates of an area in said image raster for which the information signals of said first set have a particular characteristic, a further set of said information signals then being generated from said area of said raster defined by said maximum and minimum orthogonal co-ordinates.

21. Apparatus for material analysis including:
energy generating and directing means for causing a beam of energy to fall on a spot on the surface of a sample of the material to be analysed;
detector means for detecting X-rays generated at said spot and for producing first signals representative of the energies of detected X-rays;
first accumulating means coupled to accumulate a first count of the number of said first signals each representative of an energy within a first relatively broad range of energies;
second accumulating means for accumulating a second count of the number of said first signals each representative of of an energy in an associated relatively narrow range of energies about one particular energy;
presettable means coupled to said first accumulating means and responsive, on said first count reaching a predetermined value, to control said second accumulating means to hold the value of said second count then assumed, whereby said assumed value represents a normalized ratio of said second count to said first count which normalized ratio is dependent on the proportion of a particular chemical element in said sample.

22. Apparatus as claimed in claim 21 including at least one further second accumulating means, each second accumulating means being coupled to said detector means for providing a respective said second count; each second count being a count of the numbers of said first signals representing the energy in a respective separate relatively narrow range of energy, about said particular energy and representing a respective normalized ratio.

23. Apparatus as claimed in claim 22 including at least one further first accumulating means, each first accumulating means being coupled to said detector means for providing a respective first count, the first counts being counts of the numbers of said first signals each representative of the energy within a different respective relatively broad range of such energy.

24. Apparatus as claimed in claim 23 arranged whereby, for each relatively broad range of energies for which a first count is accumulated in a respective first accumulating means, there is therewithin at least one particular energy or associated relatively narrow range of energies for which each second count is accumulated in a respective second accumulating means.

25. Apparatus as claimed in claim 24 wherein said presettable means is arranged whereby the predetermined value for at least one said first count is different from the predetermined value for at least one other first count.

26. Apparatus as claimed in claim 23 wherein each first accumulating means comprises a first discriminator device coupled to receive said first signals and operable to produce a first output signal when a first signal is representative of an energy within a respective relatively broad range of energies, and a first counter coupled to said first discriminator whereby a number of said first output signals is accumulated in said counter to provide said first count; each second accumulating means including a respective first discriminating device coupled to receive said first signal operable to produce a second output signal when a said first signal is representative of an energy within a respective relatively narrow range of energies and a second counter connected to the respective second discriminator means for accumulating a number of second output signals received thereby to provide a respective second count; said presettable means comprising a third counter and a comparator, said comparator being connected to compare a count in use held in said third counter and representing said predetermined value with the count in said first counter and operable on coincidence of the counts in the third and first counters to generate a hold signal, said comparator being connected to at least one associated second counter for latching the count held in each associated second counter at said assumed value when said hold signal is generated.

27. Apparatus as claimed in claim 26 wherein there are two of said first accumulating means, each arranged for applying a respective hold signal to at least one respective associated second counter and there being a separate presettable means for each first accumulating means.

28. Apparatus as claimed in claim 27 wherein gate means is provided coupling to the third counter of the presettable means associated with one of said first accumulating means and selectively operable to decrement the count in said third counter from an initially preset value in accordance with the number of said second output signals received from at least one of said discriminator means.

29. Apparatus as claimed in claim 28 including divisor means coupled to at least two of said second counters and operable to produce a ratio signal representative of the ratio of the assumed value of said second counts in those second counters.

30. Apparatus as claimed in claim 29 including a backscattered electron detector means for detecting backscattered electrons generated at the said spot pursuant to incidence of said beam thereon and operable in use to generate a second signal representative of intensity of such backscattered electrons.

31. Apparatus as claimed in claim 30 wherein said backscattered electron detector means includes means operable to generate said second signal by integrating an output from a backscattered electron detector device forming part of said backscattered electron detector means and delay means responsive to initiation of incidence of said beam on said spot to delay the beginning of said integration for a predetermined period.

32. Apparatus as claimed in claim 31 including means for generating an information signal representative of analysis of said sample at said spot.

33. Apparatus as claimed in claim 32 wherein said means for constructing an information signal includes digital means producing said information signal as a digital word, individual bits of which word are representative of at least selected ones of said second signal magnitude, said word including individual bits and collectively representing at least one of the intensity of said second signal and of one of said assumed values of said second count of at least one of said ratios of said second counts.

34. Apparatus as claimed in claim 33 including means for directing said beam in a raster pattern on said sample said raster pattern being made up of an array of spots and said apparatus being operable to generate a separate information signal at each spot in said raster.

35. Apparatus as claimed in claim 34 including means for storing information signals for each said spot.

36. Apparatus as claimed in claim 35 including comparator means operable to compare the second signal generated for two successive spots in said raster pattern and operable to inhibit generation of at least one component of the information signal for the second occurring of these successive spots or at least to inhibit storage thereof on detection of a condition of substantial identity between the second signals for the two successive spots.

37. Apparatus as claimed in claim 35 including comparator means for comparing two successively generated information signals and for suppressing storage of one thereof on detection of a condition of substantial identity therebetween.

38. Apparatus as claimed in claim 34 including means for accumulating second counts and/or said second signals for numerous said spots to provide accumulation signals representative of average analysis of said sample over said raster or part thereof.

39. Apparatus as claimed in claim 34 operable to generate a first set of said information signals by scanning said raster and to generate therefrom maximum and minimum orthogonal coordinate signals representing an area in said raster for which the information signals of said first set have a particular characteristic and operable to generate a further set of said information signals from said area.

40. Apparatus as claimed in claim 30 wherein said backscattered electron detector means includes an array of backscattered electron detectors together with signal combining means for combining signals generated by the detectors.

41. Apparatus as claimed in claim 40 wherein said detectors are positioned such that combined signals resulting from incidence of said beam on a single said spot are substantially independent of the slope of the surface at that spot.

42. A method as claimed in claim 2, wherein said first count consists of the sum of all or of any one or more of the second counts.

* * * * *